United States Patent
Kling et al.

[11] 4,227,321
[45] Oct. 14, 1980

[54] SAFETY WRAPPER AND STRAP

[76] Inventors: Stephen C. Kling, 1151 Warrington Rd., Deerfield, Ill. 60015; William A. Sands, 1441 Paddock, Northbrook, Ill. 60062

[21] Appl. No.: 970,240

[22] Filed: Dec. 18, 1978

[51] Int. Cl.² ............................ A43B 7/22; A43B 5/04
[52] U.S. Cl. ............................................. 36/91; 36/119
[58] Field of Search ........................... 36/91, 114, 119

[56] References Cited

U.S. PATENT DOCUMENTS

| | | | |
|---|---|---|---|
| 1,286,787 | 12/1918 | Rokahr | 36/91 |
| 3,323,232 | 6/1967 | Danowsky | 36/91 |
| 4,064,642 | 12/1977 | Vykukal et al. | 36/119 |

Primary Examiner—Patrick D. Lawson
Attorney, Agent, or Firm—Rummler & Snow

[57] ABSTRACT

A safety wrapper and strap protector encompassing the middle of the foot of a person with a trailing strap which is placed over the bottom and back of the heel when the heel is slightly elevated, extending upwardly on the back of the leg and adhesively secured thereto above the ankle to prevent injury to achilles tendon, the posterior ankle joint capsule and other structures at the posterior portion of the ankle and subtaler joint during running and gymnastic exercises.

2 Claims, 3 Drawing Figures

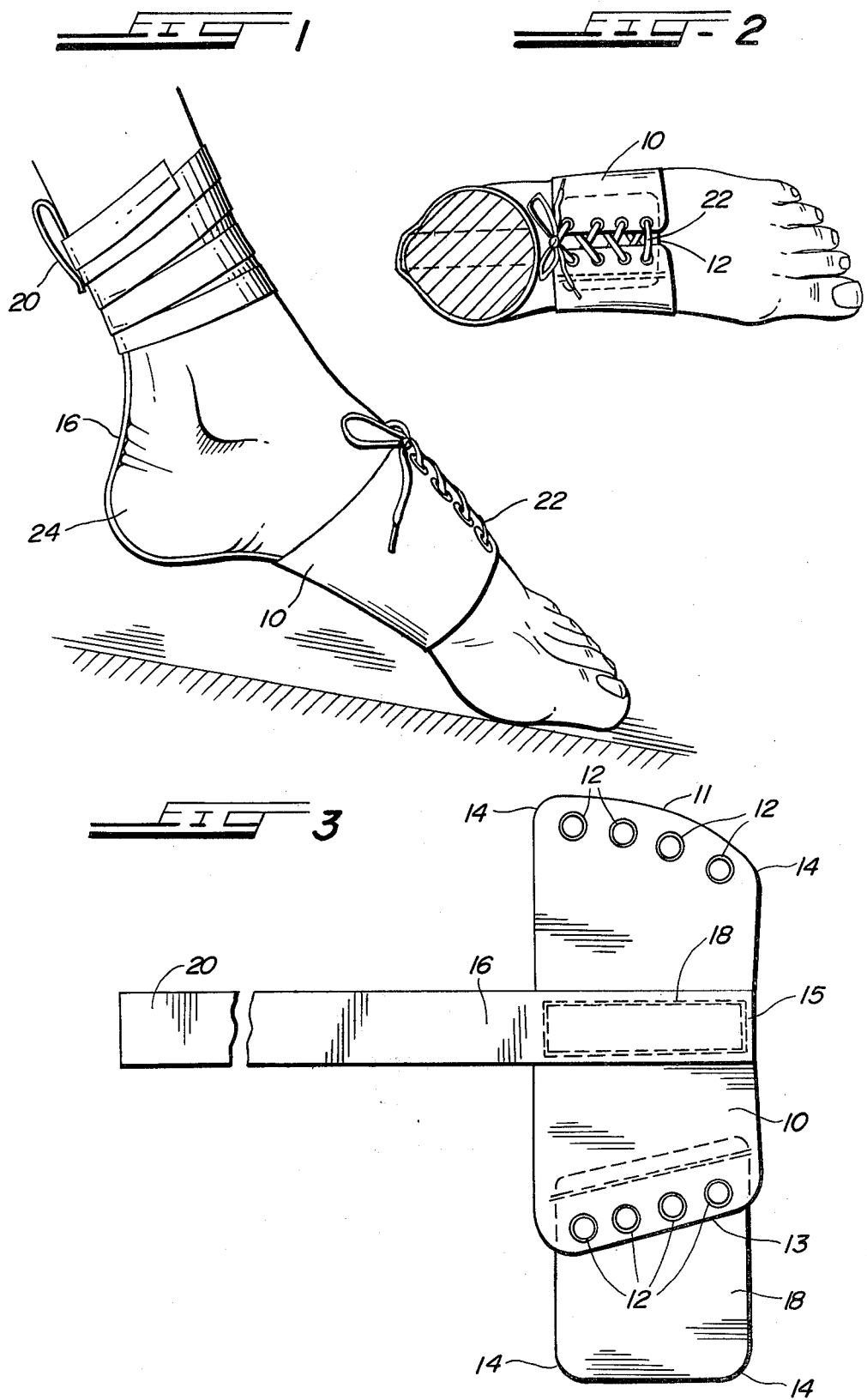

SAFETY WRAPPER AND STRAP

BACKGROUND OF THE INVENTION

While performing gymnastics, most persons use soft ballet slippers. However, when dismounting from apparatus, where height is important, or doing free exercises such as tumbling and the like on hardwood floors, as well as maneuvers in other sports, the achilles tendon, the planteris tendon, the posterior ankle and subtaler joint capsule and other structures at the posterior portion of the ankle and subtaler joint undergo severe stress both in acute phase and in chronic overuse phase leading to calf strain, tendonitis, inflammation of the joint capsule and other disabilities. It was to help prevent these serious conditions that the present invention was conceived.

BRIEF DESCRIPTION OF THE DRAWINGS

FIG. 1 is a side elevational view of a human foot with the device of the present invention incorporated thereon; FIG. 2 is a top elevational view of FIG. 1 with part of the ankle shown in cross section; and FIG. 3 is a bottom plan view of the device of the invention.

SUMMARY OF THE INVENTION

A foot wrapper device for encompassing the mid-portion of the foot having a trailing strap to pass over the bottom of the heel and upwardly against the back of the leg and anchored thereto just above the ankle when the heel is raised slightly above the floor. This device will help prevent inflammation to the ankle and subtaler joint capsule, calf strain, tendonitis and other disabilities.

DETAILED DESCRIPTION OF THE DRAWINGS

The device of the present invention comprises a main body 10 having a series of lace grommets 12 on each distal end. Also, the distal end 11 is slightly arcuate shaped while the other end 13 is angled forwardly, as seen in FIG. 3, each end terminating in rounded edges 14.

One end 15 of a strap 16 is sewn as at 18 to the bottom of the body 10 medially of the ends of said body while the other end 20 trails outwardly. A tongue 18 is secured by sewing adjacent to the end 13 of the body 10 and on the under side thereof. Thus, when the body 10 is in position around the mid-foot of the person using this device, the tongue will lie below the body and under the grommets 12.

The body is laced together by a shoelace 22, employing the grommets 12, as seen in FIGS. 1 and 2. The strap 14 trails rearwardly from the body 10 and when the heel 24 of the foot of the person to be equipped with this device is raised about two inches off the surface of the floor, the strap is drawn around the heel and brought upwardly along the back of the leg and the strap 16 is anchored to the leg by any means such as a series of adhesive tapes 19. The tapes start just above the talus bone. Additional tapes are placed adjacent each other until the tapes are securely fastened around the leg. Any remaining length of the strap is tucked in and secured by the adhesive tape. This procedure is followed for both feet. The slipper or shoe is then placed on the feet.

The device of the present invention is preferably made with buckskin, deerskin or other soft material such as split cowhide.

When an individual wearing the device of the present invention undergoes a surprise or sudden movement causing severe impact at the forepart of the foot, the device will assist in restraining the foot from an over dorsiflexed position.

Although but one specific embodiment of this invention is herein shown and described, it will be understood that details of the construction shown may be altered or omitted without departing from the spirit of the invention as defined by the following claims.

We claim:

1. A device of the class described for lessening injury by over-dorsiflexion of the foot and leg of a wearer during certain gymnastic maneuvers comprising a main elongated body having angular ends and a lower side, means for securing the ends together, an elongated tongue anchored to one end of the body on the lower side with the remaining portion extending outwardly, an elongated strap anchored at one end to said lower side of said body medially of the ends of the body with the remaining portion extending outwardly from said body where anchored, whereby said body is secured to the mid-foot of the wearer and the strap extends around the heel of the foot and upwardly along the leg and is removably anchored thereto while the heel is slightly elevated.

2. The device according to claim 1 wherein the means for securing said ends together is a lace which extends in and through grommets positioned adjacent the ends of said body while said tongue lies below the grommets and the opposite end of said body.

* * * * *